(12) United States Patent
Kuyava

(10) Patent No.: US 6,558,315 B1
(45) Date of Patent: May 6, 2003

(54) PARYLENE-COATED COMPONENTS FOR INFLATABLE PENILE PROSTHESIS

(75) Inventor: Charles C. Kuyava, Eden Prairie, MN (US)

(73) Assignee: AMS Research Corporation, Minnetonka, MN (US)

( * ) Notice: Subject to any disclaimer, the term of this patent is extended or adjusted under 35 U.S.C. 154(b) by 0 days.

(21) Appl. No.: 09/526,051

(22) Filed: Mar. 15, 2000

(51) Int. Cl.$^7$ .................................................. A61F 5/00
(52) U.S. Cl. ...................................................... 600/40
(58) Field of Search .................. 600/38–41; 623/11–12, 623/901

(56) References Cited

U.S. PATENT DOCUMENTS

| | | |
|---|---|---|
| 4,541,420 A | 9/1985 | Timm et al. |
| 4,610,690 A | 9/1986 | Tiffany |
| 4,651,721 A | 3/1987 | Mikulich et al. |
| 4,731,081 A | 3/1988 | Tiffany et al. |
| 4,773,403 A | 9/1988 | Daly |
| 4,829,990 A | 5/1989 | Thüroff et al. |
| 4,881,530 A | 11/1989 | Trick |
| 4,881,531 A | 11/1989 | Timm et al. |
| 5,295,978 A | 3/1994 | Fan et al. |
| 5,344,388 A | 9/1994 | Maxwell et al. |
| 5,545,220 A | 8/1996 | Andrews et al. |
| 5,736,251 A | 4/1998 | Pinchuk |
| 5,804,318 A | 9/1998 | Pinchuk et al. |
| 5,824,049 A | 10/1998 | Ragheb et al. |
| 5,873,904 A | 2/1999 | Ragheb et al. |
| 5,925,069 A | 7/1999 | Graves et al. |
| 5,957,965 A | 9/1999 | Moumane et al. |

FOREIGN PATENT DOCUMENTS

| | | |
|---|---|---|
| EP | 0 682 923 A1 | 11/1995 |
| EP | 0 719 582 A2 | 7/1996 |
| EP | 0 925 764 A1 | 6/1999 |
| WO | WO 94/04095 A | 3/1994 |
| WO | WO 95/18570 A | 5/1998 |
| WO | WO 00/10622 A1 | 3/2000 |

OTHER PUBLICATIONS

Parylene, A Biostable Coating for Medical Applications; Specialty Coating Systems; Mar. 1998; 6 pages.
American Medical Systems, Operating Room Manual "AMS 700™ Penile Prosthesis Production Line," 1998.
American Medical Systems, Operating Room Manual "AMS Ambicor™ Penile Prosthesis," 1995.
American Medical Systems, Operating Room Manual "AMS Sphincter 800™ Urinary Prosthesis," 1995.
American Medical Systems, Operating Room Manual "Action™ Neosphincter," 1999.

*Primary Examiner*—John P. Lacyk
(74) *Attorney, Agent, or Firm*—Faegre & Benson LLP

(57) ABSTRACT

A penile prosthesis beneficially includes components coated with parylene in order to increase product life and reduce wear. In particular, components of the inflatable cylinder benefits from having been coated with parylene. The parylene-coated cylinder components are resistant to wear generated by pinching of the cylinder when the cylinder is in a flaccid state. The parylene-coated cylinder may be formed by masking a tube of silicone (or other appropriate material) and vapor coating the silicone tube with parylene. Further, where a double walled cylinder is used, each of two tubes making up the double wall cylinder can have their surfaces coated with parylene, thus increasing cylinder life and avoiding wear.

37 Claims, 4 Drawing Sheets

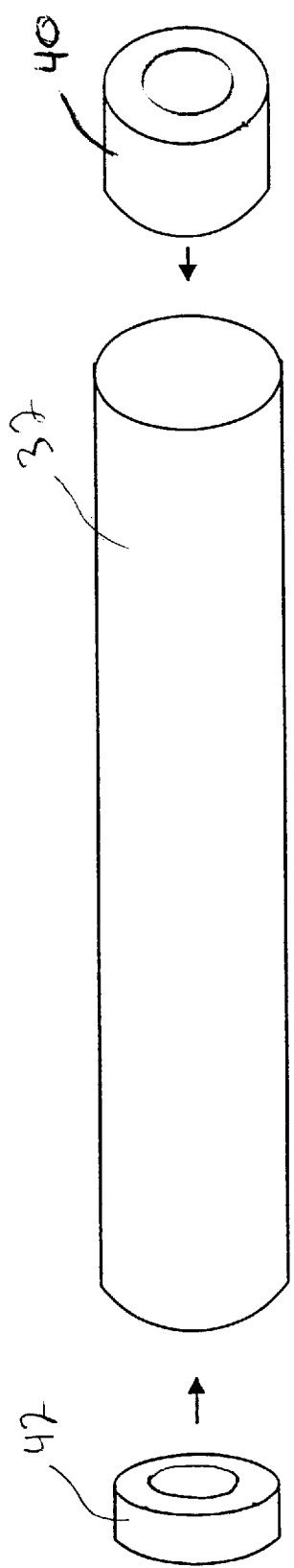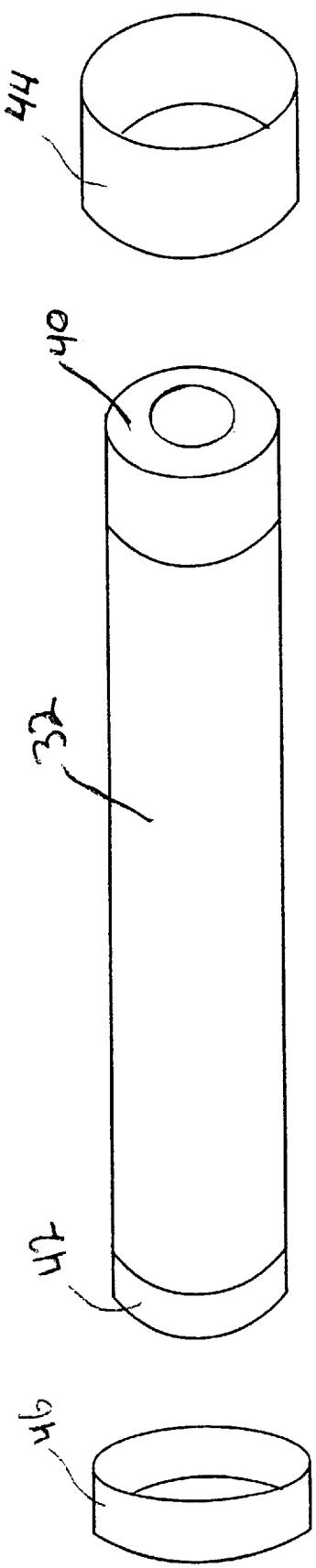
Figure 5
Figure 6

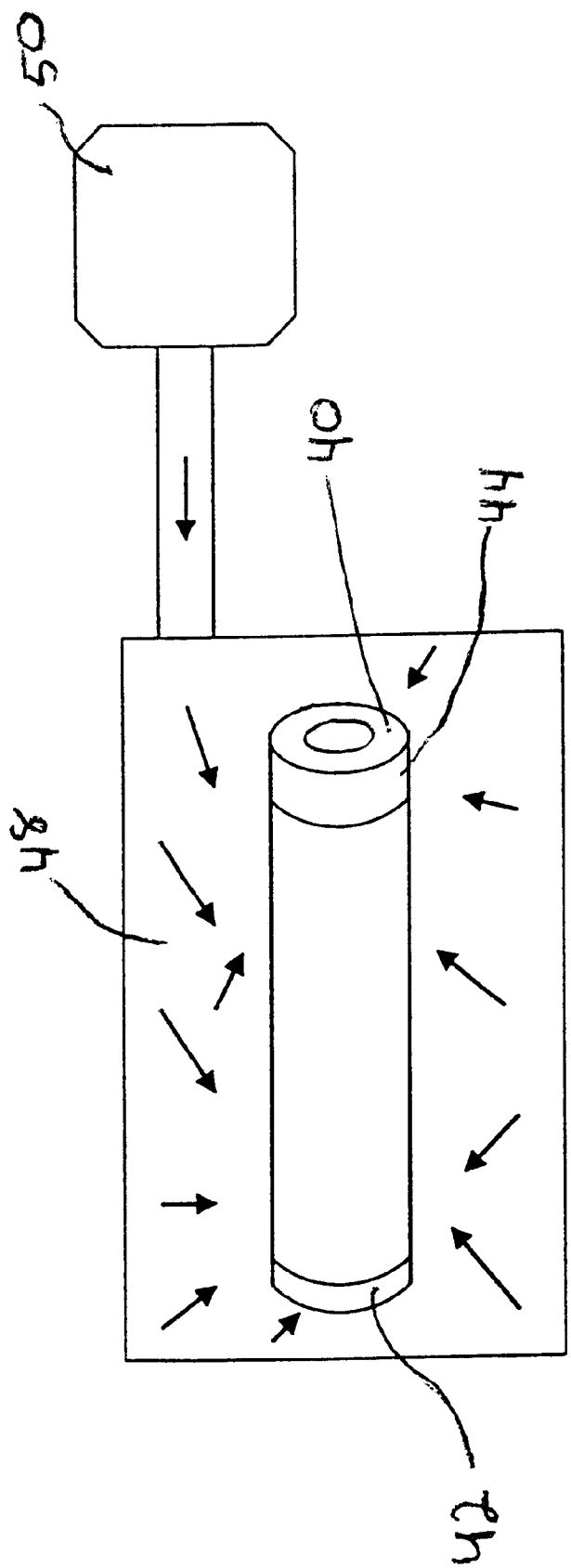

US 6,558,315 B1

PARYLENE-COATED COMPONENTS FOR INFLATABLE PENILE PROSTHESIS

BACKGROUND OF THE INVENTION

1. Field of the Invention

This invention relates generally to penile prostheses and more specifically to parylene-coated components used therefor.

2. Description of the Related Art

The implantation of a penile prosthesis is one known treatment for the condition in human males known as erectile dysfunction or ED. Once implanted, the penile prosthesis is used to artificially create an erection, thus allowing the patient to be sexually active.

Such prosthesis generally includes a pair of inflatable cylinders which are implanted, in parallel, in the patient's corpus cavernosae. The prosthetic also includes a pressurized reservoir of fluid that is implanted elsewhere in the patient's body, usually in the abdomen. A pump and valve assembly is fluidly coupled to the reservoir via reservoir tubing and the pair of inflatable cylinders are then fluidly coupled, via fluid passageways, to the pump and valve assembly. Upon actuation of the pump and valve assembly, the cylinders become pressurized due to fluid transfer from the reservoir to the pump and valve assembly and from the pump/valve to the cylinders which, in turn, causes the cylinders to become rigid. This rigidity thereby causes the desired erection.

There are several variations of such a prosthetic. For example, the cylindrical members can expand as they are pressurized, or in another variation, they may simply go from an empty, flaccid state to a full, rigid state, with no expansion of the cylinder(s). The reservoir and/or the pump assembly can also be made integral with the cylinder(s).

In order to adapt the prosthetic to the patient's anatomy, the cylinders have arcuate front and rear cap portions which mate well with the ends of the corpus cavernosae. Moreover, the caps serve to form a sealed chamber within the cylinder thus enabling the cylinder to inflate.

In order to control the expansion of the cylinder as it is inflated, a sleeve of fabric or other cloth-like material is placed around an inner tube of the cylinder. Thus, the diameter of the cylinder can only expand to a size congruent with the fabric sleeve. The use of a fabric sleeve also effectuates a uniform inflation. Typically, a second sealed outer tube is placed around the inner tube and the fabric sleeve. Thus, a typical cylinder wall includes two tubes, one within the other. Consequently, proper functioning is dependent on the correct operation of the inner tube and, in some embodiments, on the correct operation of the outer tuber as well. That is, in some cases, the area around the outer tube is used for fluid transfer and/or storage. A fabric sleeve may also be used with those types of cylinders that do not expand when filled, but simply become rigid.

The double walled structure is an efficient arrangement. One potential issue is the continuous contact between each of the tubes and the fabric. The prosthetic exists in a relaxed or flaccid state a majority of the time and thus the inner and outer tubes are in contact with the fabric a majority of the time. The specifics of this situation are elaborated below.

In order to provide comfort and a better sense of normalcy to the patient, the prosthetic is made from materials that allow the prosthetic to bend and be flexible when in the flaccid state. Such bending, however, may lead to the formation of a crease in the walls of the double-walled or single-walled device. This crease terminates in bend corners that are areas of stress and highly localized areas of contact between the cylinder's inner and outer tubes and the fabric sleeve. Consequently, as the flaccid cylinder is bent from side to side or generally moved about a central axis due to normal movement of the patient, the bend corners will likewise travel thus resulting in pockets of the cylinder contacting and moving across each other. This results in a movement of the corners which causes portions of the tubes to contact (and move across) each other. There is also a potential element of material fatigue as the various materials are repeatedly stressed and unstressed.

Moreover, since the crease generally occurs in the same location on the cylinder, the same areas of contact are repeatedly moved across each other. Over time, this repeated contact and movement may lead to wear, abrasion, and fatigue.

Typically, the tubes are formed from a versatile material such as silicone or polyurethane which are medically safe and provides the necessary degree of structural reliability. It has been found that silicone has a high coefficient of friction and can be somewhat tacky. As a result, when silicone contacts itself or some other surface, it can bind and resist movement. Indeed, this frictional engagement could cause the contacting surfaces to wear at these contacting locations and eventually could potentially cause the tubing to wear and fatigue.

For the same reasons, similar situations may be encountered with other components of the prosthesis. The fluid passageways, the reservoir, the housing for the pump and valve assembly are all typically made from silicone. Thus, in any instance where the silicone surfaces of these components are caused to bend, to contact other silicone surfaces, or to fatigue, similar situations of wear may be encountered.

SUMMARY OF THE INVENTION

The present invention provides a penile prosthesis which has components formed from silicone or similarly flexible material which are coated with a material that increases the strength of the component while also reducing its coefficient of friction. When corners are formed in the flaccid cylinder, for example, increased wear tolerances are exhibited by allowing the components of the cylinder to smoothly move against each other. The coating material allows one surface of the cylinder to slide smoothly against another surface. Thus, wear due to abrasion is significantly diminished. Furthermore, the coating material minimizes fatigue and resists contact stresses.

In a preferred embodiment, both the inner and outer surfaces of the tube(s) of the cylinder are coated with a very thin layer of parylene. Parylene is an ideal material for this purpose in that it provides a very strong and wear resistant surface, is relatively slippery, is fatigue resistant, and allows for repeated expansion and contraction with no negative effects.

To form the components of the cylinder (or any other tubular component) of the preferred embodiment of the present invention, a silicone tube is sized. Both the inner and outer surfaces of each end portion are then masked. The masking can be done by inserting sections of rigid silicone into the ends of the silicone tube. This rigid insert has an outer diameter approximately equal to the inner diameter of the silicone tube. A wrapping, such as shrink-wrap (heat shrink tubing), is then placed over the outer diameter of the silicone tube, to correspond with the rigid insert. The shrink-wrap is then heated causing it to shrink. This, in turn, causes the silicone tube to compress the rigid insert, thus generating a portion of the silicone tube that is sealed between the rigid insert and the outer wrapping.

The masked tube is then placed in a vapor deposition chamber where vaporized parylene is introduced into the environment. In a known way the vaporized parylene simultaneously coats both the inner and outer surfaces of the silicone tube to a predetermined thickness. The coated silicone tube is then removed from the deposition chamber and the rigid inserts and shrink-wrap are removed from the coated silicone tube. Appropriate end caps are attached and adhered to the non-coated portions, thus forming a complete cylinder. Alternatively, coating just the inner or the outer surface will also lead to increased wear characteristics.

In addition, any of the other components of the penile prosthesis could likewise be coated, thus realizing increased wear characteristics.

For those cylinders utilizing a double wall structure, it is optimal to coat the inner and outer surfaces of both tubes forming the completed cylinder. Increased wear characteristics are achieved, however, even when just the inner or outer surfaces are coated.

The present invention includes applying a coating of a material such as parylene to one or more components of a penile prosthesis. This is applicable to virtually any type or style of prosthesis. Namely, whether a single or double walled cylinder is utilized, whether expandable or non-expandable cylinders are utilized, or whether the components (cylinders, pump assembly, reservoir, etc.) are separate or integral, the coating will be advantageous.

Yet another aspect of the present invention is the application of parylene, or a similar material to a variety of implantable devices, commonly formed from silicone or a like material. As specifically detailed herein as the preferred embodiment, a penile prosthesis having connected but separate components (cylinders, reservoir, pump) will benefit greatly by having a coating of a material such as parylene applied to one or more of those components. In addition, many penile prosthetics come in different configurations. A reservoir may be made integral with the cylinder, or all of the components may be made from one integral unit. As referred to herein, the penile prosthesis is meant to include any and all of these various forms, as they may all benefit from the application of a material such as parylene.

In addition to the penile prosthesis, other implantable devices are commonly formed from silicone or other flexible materials and can benefit from the application of a coating of parylene. For example, testicular implants are sometimes implanted into a male patient to return a sense of normalcy to that patient. Such implants may be implanted during the implantation of the penile prosthesis to minimize surgical exposure. Testicular implants can be formed as elliptical or oval silicone blocks. These blocks are generally solid, but could be fluid filled. In either event, the application of parylene of a like material will reduce the effects of frictional engagements as the implants are moved about. In addition, the coating may serve to contain the material forming the implant, thus preventing leakage into the patients. For this reason, it is also desirable to apply parylene to silicone breast implants. The parylene will serve to contain the fluid filled implant and will reduce the abrasive effects cause by the normal movement of the implant.

Another type of implantable device within the scope of the present invention is an artificial sphincter. An artificial sphincter is somewhat similar in form and function to the penile prosthesis. Namely, a reservoir and a pump are provided and are coupled to an inflatable member. The inflatable member is positioned so that when inflated, it exerts pressure on the urethra or bladder neck, in the case of artificial urinary sphincters, or the rectum in the case of artificial bowel sphincters. As pressure is applied, the rectum or the urethra is effectively sealed, thus preventing incontinence. These devices can come in various forms; i.e., those with separate components connected by tubing or those having certain parts combined into an integral unit (pump combined with reservoir). Whatever their form, it is advantageous to coat the various components with parylene or a like material. The coating serves to minimize the effects of frictional engagement and will increase the life expectancy of the product.

BRIEF DESCRIPTION OF THE DRAWINGS

FIG. 5 is a side-elevational view of a silicone tube used to make a cylinder in a penile prosthesis wherein front and rear rigid inserts are being inserted inside the tube to form a mask.

FIG. 6 is s side-elevational view of a silicone tube used to form a cylinder in a penile prosthesis wherein front and rear inserts have been inserted into the tube and front and rear shrink wrappings are being placed over the outer circumference of the ends of the tube.

FIG. 7 is a schematic diagram illustrating a masked silicone tube within a vapor deposition chamber.

DETAILED DESCRIPTION OF PREFERRED EMBODIMENTS

Figure 1:
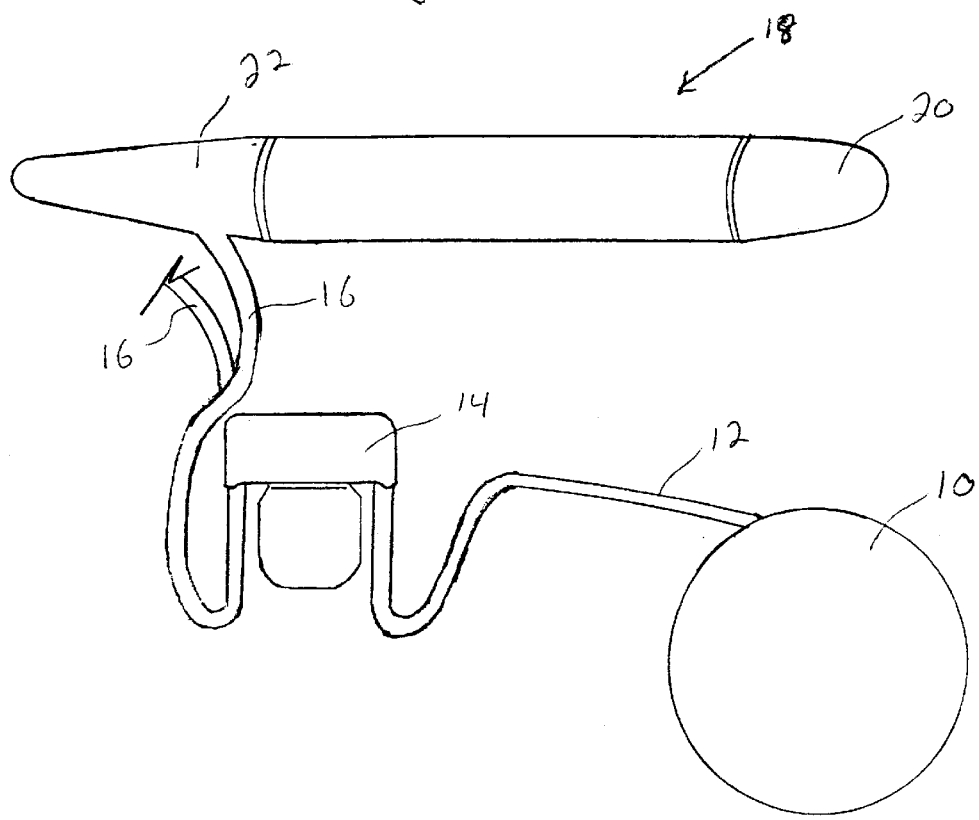
FIG. 1 is a side-elevational view of a penile prosthesis system including a reservoir, a pump and valve assembly, and a cylinder.

Referring to FIG. 1, the penile prosthesis of the present invention includes a pair of cylinders 18 that are selectively inflated by actuating pump and valve assembly 14 thus transferring fluid from reservoir 10, through pump and valve assembly 14, and into cylinder 18 under pressure. (Only one cylinder of the pair is illustrated). As such, cylinder 18 will inflate thus producing the desired effect. When the user desires to deflate cylinder 18, pump and valve assembly 14 is opened, thus allowing the pressurized fluid to retreat from cylinder 18 back into reservoir 10. This returns cylinder 18 to its flaccid state. In previous penile prostheses, cylinder 18 has usually been composed solely of polyurethane, silicone or a combination of the two.

It is to be understood that the prosthesis illustrated is only meant to be representative of the variety of penile implants currently used. That is, the illustrated implant will expand upon inflation and has separate components interconnected by tubing. Other types of implants provide for cylinders that do not expand (in any direction) but simply become rigid. There are also implants having a reservoir formed integrally with one or both of the cylinders. Likewise, the pump can be formed integrally with the reservoir and/or the cylinders. It is to be understood that all of these variations are within the scope of the present invention and are referred to generally and collectively as a penile prosthesis.

Figure 3:
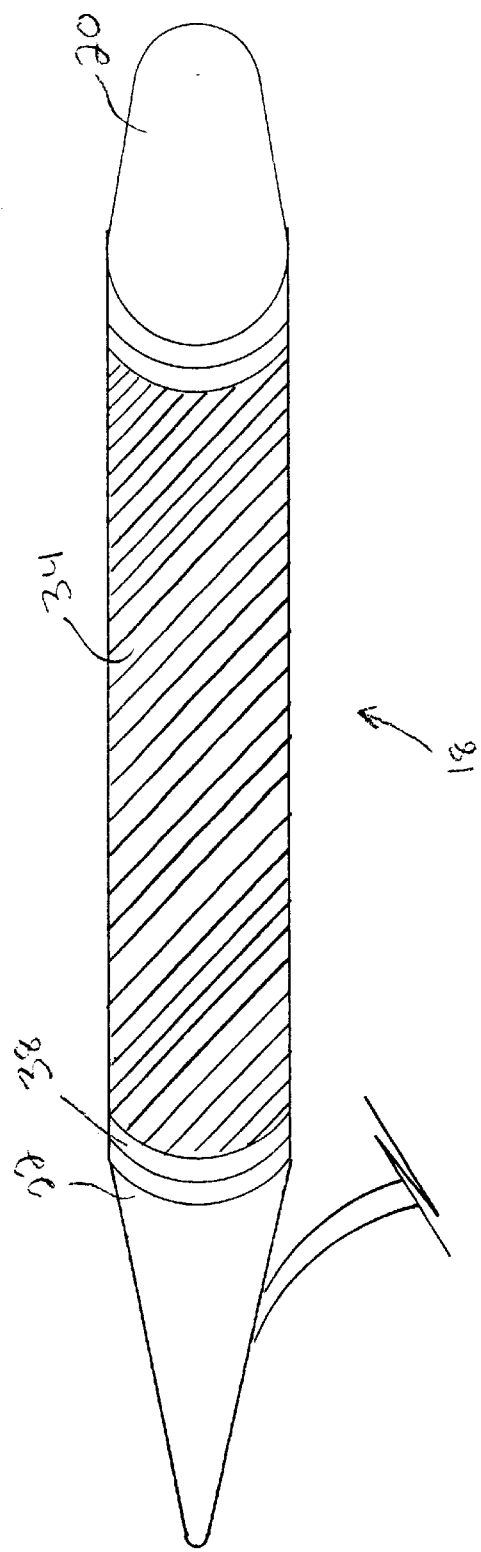
FIG. 3 is a side-elevational view of a cylinder with a parylene-coated silicone tube with end caps in place.

Referring to FIG. 3, cylinder 18 is shown to be formed from silicone and has a layer of parylene deposited over a substantial portion of its inner and outer surfaces. The parylene coating is represented by hatched lines (in FIGS. 3 and 4). FIG. 3 illustrates the completed cylinder 18 having front and rear end caps 20 and 22 attached thereto. As shown, the end caps 20 and 22 are not coated with parylene. These portions of cylinder 18 are less likely to contact other portions of the cylinder 18, thus minimizing the frictional engagement which leads to wear. The end caps 20 and 22 are also thicker and more rigid than the tubing, again reducing the risk of wear. However, to provide the highest level of security and wear resistance, end caps 20 and 22 (or a portion thereof) could likewise be coated.

Often, double walled cylinders are used wherein each tube of the cylinder (inner and outer) may have its inner and outer surfaces coated. Though not illustrated, double walled cylinders will have a layer of fabric between the two wall portions. This fabric could also be coated on one or both sides with parylene, reducing the coefficient of friction of the material. This coated fabric could then be utilized in the same fashion. Alternatively, the coated fabric could eliminate the need for the outer tube.

Figure 4:
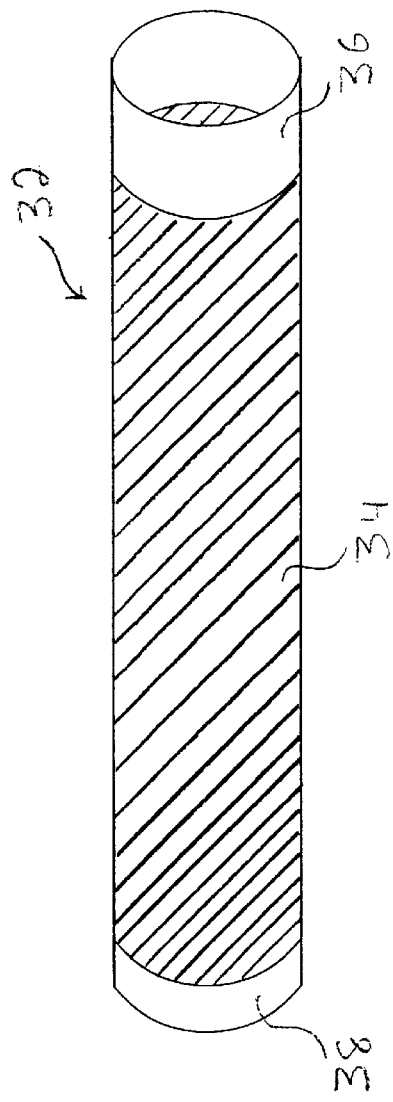
FIG. 4 is a side-elevational view of a silicone tube used to make the cylinder of the penile prosthesis, which has been coated with parylene.

Referring to FIG. 4, cylinder 18 is shown having end caps 20 and 22 removed. The silicone tube 32 has had parylene deposited on its inner and outer surfaces on all portions except front end section 36 and rear end section 38 which have no parylene deposited on either the inner or outer surfaces. Front and rear end sections 36 and 38 are left uncoated so that end caps 20 and 22 can be firmly secured to the silicone tube 32. (Likewise, if caps 20 and 22 were to be coated, a corresponding portion of the caps 20 and 22 would be left uncoated.) If parylene were applied in these areas, the strength of the bond between the tube 32 and the end caps 20 and 22 would be greatly reduced as parylene does not work well with many of the silicone adhesives. This assumes an end cap structure which is bonded to the silicone tube 32. Many variations are conceivable, thus altering the masking parameters. For example, if the end cap is only bonded to an inner surface of the tube 32, the entire outer surface of the tube 32 could be coated in parylene. Similarly, if the cap is only bonded to the outer surface, the entire inner surface can be coated. In the preferred embodiment, the tube 32 is masked as illustrated and the caps 20 and 22 are bonded to tube 32.

Various other adhesion techniques could be employed, bonding the caps 20 and 22 to the parylene coating. This may include coating the end caps 20 and 22 with parylene prior to bonding. When handling any other component, appropriate masking should be employed. Any tubular structure could be masked as described below. Larger components such as reservoir 10 or pump and valve assembly 14 have different requirements, thus the coating and masking characteristics will vary. For example, all surfaces of the reservoir 10 can be coated except where the reservoir tubing 12 will be connected. This is due to the same parylene/silicone adhesive issues described above.

Figure 2:
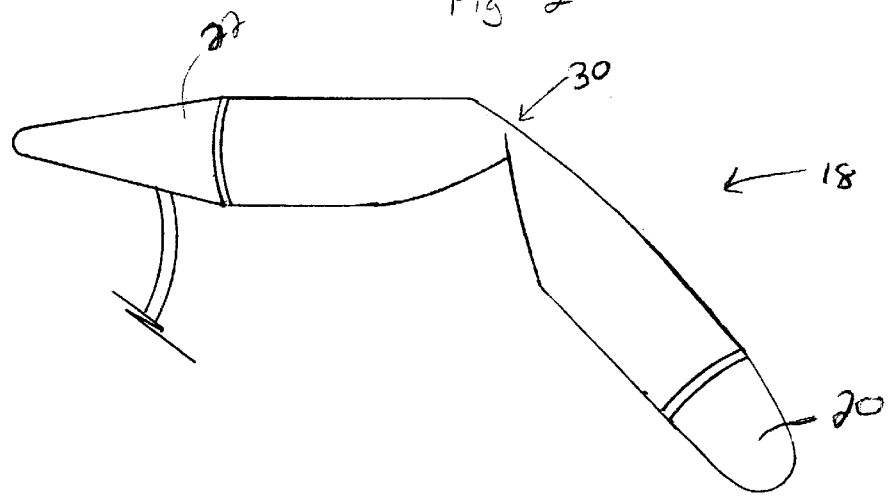
FIG. 2 is a side-elevational view of a penile prosthesis cylinder in its flaccid state.

When the parylene-coated silicone tube 32 illustrated in FIG. 3 is in the condition shown in FIG. 2, i.e. flaccid, corners 30 are formed at the pinch points. (It is noted that any or all of the components shown in FIGS. 1 and 2 could be coated with parylene, thus the coating is not separately shown by hatched lines.) In the flaccid state, a crease line is created extending across the cylinder terminating in a pair of bend corners 30. As the cylinder naturally moves (in its flaccid condition) the crease line changes its location and orientation, thus causing the bend corners 30 to be translated or moved along the cylinder due to normal movement of the patient. However, the parylene coating slides smoothly over itself or any adjacent component it may come into contact with, thus greatly reducing frictional wear. In addition, parylene also has greater strength than silicone to better resist contact and fatigue stresses.

Parylene is a unique material forming a high molecular weight, linear, crystalline polymer coating having an all carbon backbone. During the vapor deposition process, parylene never enters the liquid state, thus an extremely continuous and even coating occurs. Parylene has excellent dry film lubricant characteristics as indicated by its coefficient of friction, which approaches polytetrafluoroethylene. Parylene will have a coefficient of friction approximately $\frac{1}{10}$ that of silicone, when the parylene exists in a 2 $\mu$m layer. Parylene is superior in its ability to resist wear and abrasion. While various parylene variations are available and each is applicable herein, parylene N seems to be the most advantageous to use, as a preferred embodiment.

When inflated, the cylinder 18 is caused to expand or at least become rigid. As such, the layers of parylene on or within cylinder 18 must likewise expand. Parylene is ideal in this situation in that it will expand without breaking and once the cylinder 18 is deflated, will return to its original configuration. In actuality, tiny structures appear in the parylene that resemble cracks in the coating. These are not actually cracks, but areas of local yielding and this characteristic allows the coating to be very effective. While parylene is ideally suited for this application, a wide variety of other materials could be used equally well. Such alternate materials need to produce a relatively smooth coating having a sufficiently high degree of dry film lubricity, which will not bind when it is caused to contact other portions of the tube and is able to be repeatedly expanded and then returned to its original configuration. The material should be relatively strong, to withstand the repeated contact, and have good wear characteristics so that a long lifetime is achieved.

Any suitable method of application may be used to apply the parylene or an alternative material to any of the components of the prosthesis. In a preferred form (for tubular components), the silicone tube is first masked as shown in FIG. 5. Silicone tube 32 is cut to length and front and rear silicone inserts 40 and 42 are inserted within the inner circumference of silicone tube 32. The front and rear inserts 40 and 42 are sized to create the appropriate area for the adhesion of the end caps 20 and 22. As shown in FIG. 6, the silicone tube then has front and rear wrappings 44 and 46 placed over the outer ends of the silicone tube 32. Any such suitable wrappings are appropriate. For example shrink wrapping or heat shrink tubing is used and after application to the ends, the shrink-wrapping is heated thus conforming closely to the size and shape of the silicone tube 32. The compression of the shrink-wrap also clamps the silicone tube 32 around the inserts 40 and 42, thus forming a barrier which prevents vapor deposition. Forming inserts 40 and 42 from silicone is advantageous in that parylene bonds extremely well to silicone. Thus, when inserts 40, 42 are removed, a clean break is formed in the parylene coating.

Previous masking techniques usually include applying a layer of liquid latex as a mask, then peeling off the latex after the application of parylene. This is unacceptable in some cases, due to the likelihood of a patient having an allergic reaction to the latex. The latex will also discolor the silicon, giving an inferior appearance. It is possible to use a synthetic liquid latex as the mask. It is also possible to use synthetic latex as the outer mask and the tubular inserts 40 and 42 as the inner mask. Since synthetic latex is water based, it will shrink upon drying, thus sealing the silicone tube 32 against the inserts 40 and 42.

The masked silicone tube 32 is then placed into a vapor deposition chamber 48 as shown in FIG. 7. Parylene or any other suitable material is then vaporized in the vaporization chamber 50 and caused to enter the deposition chamber 48. In a known way, the vaporized parylene is caused to deposit itself on the silicone tube 32. The vaporized parylene evenly coats both the inner and outer circumference of the silicone tube 32 and all areas that are unmasked. The thickness of the parylene coating is dependent on the time the silicone tube 32 remains in deposition chamber 48. The parylene should be coated on the silicone tube 32 to a thickness of between 0.000040–0.000120". Ideally, the parylene should be about 0.000040–0.000080" with a layer of 0.000060" being optimal in the preferred embodiment. Too thin of a layer will not yield the desired wear characteristics nor will it yield the desired lubricity. Too thick of a layer will make the tube too stiff and will also reduce the wear characteristics.

Once the appropriate level of vapor deposition has occurred, the silicone tube 32 is then removed, the masking elements are removed, and end caps 20 and 22 are appropriately adhered to each end. The completed cylinder 18 is then attached to the remaining components of the penile prosthesis and is ready for implantation. If a double walled cylinder is desired, the completed tube 18 is then inserted into another coated tube 32. End caps 20 and 22 are then affixed to the ends of the outer tube 32, thus forming the double walled structure. Optimally, all of the major surfaces of each tube 32 (excluding any desired masked areas) will be coated with parylene or a like material. However, various surfaces can be left uncoated to reduce cost and material issues. For example, coating the cloth barrier between the inner and outer cylinders may be sufficient to prevent wear, without those surfaces being coated. This will depend on the particular materials and configurations chosen.

Though cylinder 18 has been described as being coated with parylene or a like material, any of the components of the penile prosthesis would benefit by having a similar coating. In particular, fluid passageways 16 and reservoir tubing 12 could be optimized by such a coating. It is within the scope of the present invention to apply parylene to fluid passageways 16, reservoir tubing 17, reservoir 10, pump assembly 14, and of course cylinders 18. Namely, it is advantageous to apply parylene to any of the components of the implant. As previously described, these components are often subjected to frictional wearing. Currently, a portion of these smaller diameter components are covered in polytetrafluoroethylene to assist the surgeon in implantation. A parylene coating would increase the wear characteristics of these components and could be applied in a similar fashion to that described above for the cylinders 18. The pump and valve assembly 14 and/or the reservoir 10 can also benefit from being coated. This will reduce wear when any of the components contact any other component, when the components are being manipulated by the patient, and when the tubes or reservoir are flexing against themselves or the surrounding tissue.

Though not separately illustrated, the above described process is also applicable to other implantable devices. For example, artificial sphincters, testicular implants, and breast implants can benefit from having a coating of material, such as parylene applied thereto.

Those skilled in the art will further appreciate that the present invention may be embodied in other specific forms without departing from the spirit or central attributes thereof in that the foregoing description of the present invention discloses only exemplary embodiments thereof, it is to be understood that other variations are contemplated as being within the scope of the present invention. Accordingly, the present invention is not limited in the particular embodiments which have been described in detail therein. Rather, reference should be made to the appended claims as indicative of the scope and content of the present invention.

What is claimed is:

1. A multi-component penile prosthesis comprising one or more components having flexible expanding and contracting surfaces coated on at least one contacting surface with a parylene material adapted to a) expand and return to an original configuration, b) reduce the coefficient of friction of the contacting surface, and c) prevent or inhibit wear or degradation of the flexible expanding and contracting surface at bend corners or pinch points of crease lines associated with folding or bending of the one or more components.

2. The penile prosthesis of claim 1 comprising a flexible cylinder coated on both an inner surface and an outer surface with parylene.

3. The penile prosthesis of claim 1 wherein the entire inner and outer surfaces of the components arc coated with parylene material.

4. The penile prosthesis of claim 1 wherein a portion of the components are uncoated while the remainder of the inner and outer surfaces of the components are coated with parylene material.

5. The penile prosthesis of claim 1, further comprising:
  a flexible fluid passageway coupling a pump and valve assembly to a flexible cylinder, wherein the fluid passageway is at least partially coated with parylene.

6. The penile prosthesis of claim 1, further comprising:
  a flexible reservoir tube coupling a reservoir to a pump and valve assembly, wherein the reservoir tube is at least partially coated with parylene.

7. The penile prosthesis of claim 2 wherein the cylinder is made of silicone.

8. The penile prosthesis of claim 2 wherein the cylinder is made of polyurethane.

9. The penile prosthesis of claim 6 wherein the reservoir is at least partially coated with parylene.

10. The penile prosthesis of claim 5 wherein the pump and valve assembly is at least partially coated with parylene.

11. The penile prosthesis of claim 2 wherein the cylinder further comprises a front and rear end cap.

12. The penile prosthesis of claim 11 wherein the front and rear end cap are coated with parylene.

13. The penile prosthesis of claim 1, wherein the coating is parylene between 0.00004"–0.000120" thick.

14. The penile prosthesis of claim 1, wherein the coating is parylene between 0.00004"–0.00008" thick.

15. The penile prosthesis of claim 1, wherein the coating is parylene about 0.00006" thick.

16. The penile prosthesis of claim 1 comprising a reservoir and at least one flexible cylinder formed as a single, integral assembly.

17. A penile prosthesis component comprising an inflatable, flexible expanding and contracting cylinder wherein the cylinder is coated on at least one contacting surface with a parylene material adapted to a) expand and return to an original configuration, b) reduce the coefficient of friction of the contacting surface, and c) prevent or inhibit wear or degradation of the flexible expanding and contracting cylinder at bend corners or pinch points of crease lines associated with folding or bending of the cylinder.

18. The penile prosthesis of claim 17 wherein the cylinder is coated on both an inner and outer surface.

19. The penile prosthesis of claim 17 wherein the entire inner and outer surface of the cylinder is coated.

20. The penile prosthesis of claim 17 wherein a portion of the cylinder is uncoated while the remainder of the inner and outer surfaces of the cylinder are coated.

21. The penile prosthesis of claim 17, further comprising:
a fluid passageway coupling a pump and valve assembly to the cylinder, wherein the fluid passageway is at least partially coated with the material.

22. The penile prosthesis of claim 17, further comprising:
a reservoir tube coupling a reservoir to a pump and valve assembly, wherein the reservoir tube is at least partially coated.

23. The penile prosthesis of claim 22 wherein the reservoir is at least partially coated with the material.

24. The penile prosthesis of claim 17 wherein the cylinder is made of silicone.

25. The penile prosthesis of claim 17 wherein the cylinder is made of polyurethane.

26. The penile prosthesis of claim 17 wherein the cylinder further includes a front and rear end cap.

27. The penile prosthesis of claim 23 wherein the front and rear end cap are coated with parylene.

28. A method of making a wear resistant cylinder for a penile prosthesis comprising i) providing a length of flexible expandable and contractible tubing, ii) coating at least a portion of a contacting surface of the tubing with a parylene material adapted to expand and return to an original configuration, to reduce the coefficient of friction of the contacting surface, and to prevent or inhibit wear or degradation of the flexible expandable and contractible tubing at bend corners or pinch points of crease lines associated with folding or bending of the tubing and iii) sealing the ends of the tubing.

29. The method of claim 28, wherein the tubing is silicone.

30. The method of claim 28, wherein the tubing is polyurethane.

31. The method of claim 28 wherein an inner and outer surface of the tubing is coated.

32. The method of claim 28 further comprising:
masking a portion of the tubing to prevent a masked portion of the tubing from being coated.

33. The method of claim 32 wherein the masking step comprises:
inserting an inner insert into at least a portion of the tubing and wrapping an outer member around at least a portion of the tubing.

34. The method of claim 33 wherein the outer member is shrinkable material which shrinks in diameter when heated.

35. The method of claim 33 wherein the outer member is synthetic latex.

36. The method of claim 28 wherein coating includes placing the tubing into a vapor deposition chamber and introducing a precursor of the parylene material as a vapor into the chamber.

37. The method of claim 28 where sealing the ends includes affixing a front and rear cap to the tubing.

* * * * *

UNITED STATES PATENT AND TRADEMARK OFFICE
CERTIFICATE OF CORRECTION

PATENT NO.    : 6,558,315 B1
DATED         : May 6, 2003
INVENTOR(S)   : Charles C. Kuyava It is certified that error appears in the above-identified patent and that said Letters Patent is hereby corrected as shown below:

<u>Column 8,</u>
Line 22, please replace "arc" with -- are --.

Signed and Sealed this

Fifth Day of August, 2003

JAMES E. ROGAN
*Director of the United States Patent and Trademark Office*